United States Patent
Oliveira et al.

(10) Patent No.: US 6,310,961 B1
(45) Date of Patent: *Oct. 30, 2001

(54) DISPOSABLE SLEEVE ASSEMBLY FOR SOUND CONTROL DEVICE AND CONTAINER THEREFOR

(75) Inventors: Robert J. Oliveira, Maplewood; Martin P. Babcock, White Bear Lake; Davis W. Chamberlin, St. Paul, all of MN (US)

(73) Assignee: Hearing Components, Inc., Oakdale, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/164,852

(22) Filed: Oct. 1, 1998

Related U.S. Application Data

(63) Continuation-in-part of application No. 09/050,203, filed on Mar. 30, 1998.

(51) Int. Cl.⁷ .................................................... H04R 25/00

(52) U.S. Cl. ........................ 381/328; 381/330; 181/130

(58) Field of Search ....................... 381/309, 322, 381/324, 325, 327, 328, 330, 370, 371, 380, 382, 60; 181/129, 130, 135; 379/430; 2/209

(56) References Cited

U.S. PATENT DOCUMENTS

| | | | |
|---|---|---|---|
| 2,453,238 | 11/1948 | Locke, Jr. ............................. | 206/16 |
| 3,983,336 | 9/1976 | Malek et al. ......................... | 179/107 |
| 4,420,657 | 12/1983 | Larkin ................................. | 179/156 A |
| 4,466,539 | 8/1984 | Frauenhoffer ........................ | 206/370 |
| 4,677,679 | 6/1987 | Killion ................................. | 381/74 |
| 4,724,922 | 2/1988 | Kalayjian ............................. | 181/135 |
| 4,880,076 | 11/1989 | Ahlberg et al. ...................... | 181/130 |
| 4,969,534 | 11/1990 | Kolpe et al. ......................... | 181/130 |
| 5,002,151 | 3/1991 | Oliveira et al. ...................... | 181/130 |
| 5,031,219 | 7/1991 | Ward et al. .......................... | 381/68.6 |
| 5,201,007 | 4/1993 | Ward et al. .......................... | 381/68.6 |
| 5,401,920 | 3/1995 | Oliveira .............................. | 181/135 |
| 5,402,887 | 4/1995 | Shillington ......................... | 206/366 |
| 5,415,315 | 5/1995 | Ramierez ............................. | 220/346 |

(List continued on next page.)

*Primary Examiner*—Huyen Le
(74) *Attorney, Agent, or Firm*—Crompton, Seager & Tufte, LLC

(57) ABSTRACT

A simple and inexpensive sleeve assembly that is easy to apply to and remove from the distal end portion of a sound control device and can be adapted to provide circumferential contact with a user's ear canal to control sound delivered to that ear canal at a desired level, to provide a cerumen guard at the end of a sound deliver tube included in the sound control device, or to provide both of those functions. The sleeve assembly comprises a first layer of flexible material (e.g., sound attenuating slow recovery foam, closed cell foam, open cell foam, reticulated open cell foam, or non-foamed polymeric material depending on the requirements of the sound control device on which the sleeve assembly is used) having a periphery that can be adapted to make partial or complete contact with or conform to the car canal of a user into which the sleeve assembly is inserted, or to make little or no contact with that ear canal. A stiff resiliently flexible attachment member having a through opening is fixed to one surface of the first layer. The first layer of material can have a hole between its first and second surfaces aligned with the opening in the attachment member to afford movement of a knob-like part at the distal end portion of a sound control device through the first layer and the opening in the attachment member, or alternatively, the knob-like part can be moved through the opening in the attachment member from its side opposite the first layer. The knob-like part and the area circumjacent to the opening in the attachment member then cooperate to provide complementary interlocking holding of the sleeve assembly on the end portion of the sound control device.

31 Claims, 10 Drawing Sheets

U.S. PATENT DOCUMENTS

| | | | |
|---|---|---|---|
| 5,643,188 | 7/1997 | Oliveira | 602/54 |
| 5,654,530 | 8/1997 | Sauer et al. | 181/130 |
| 5,682,020 | 10/1997 | Oliveira | 181/130 |
| 5,701,348 | 12/1997 | Shennib et al. | 381/68.6 |
| 5,712,453 | 1/1998 | Bungardt et al. | 181/135 |
| 5,887,070 * | 3/1999 | Iseberg et al. | 381/328 |
| 5,920,636 * | 7/1999 | Oliveira et al. | 381/328 |

* cited by examiner

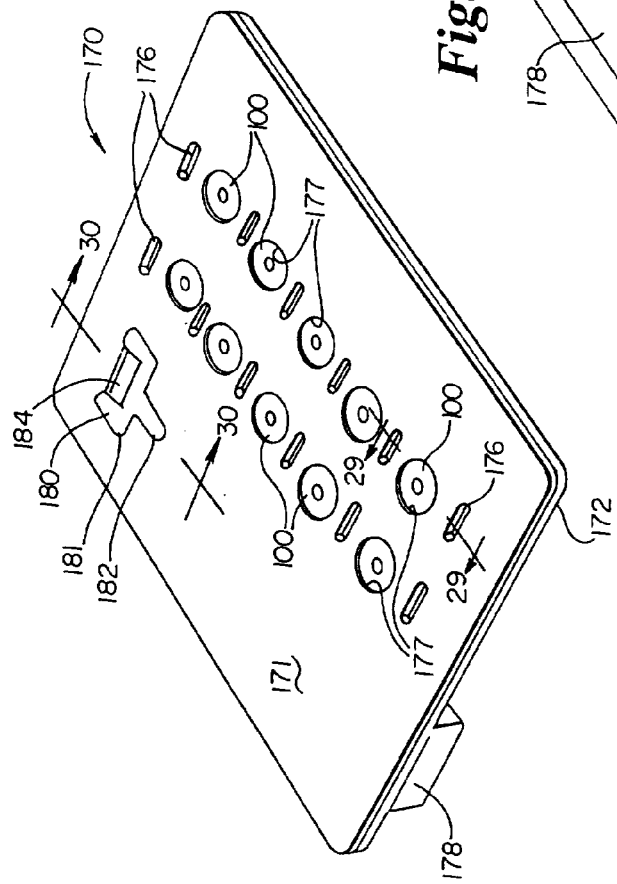
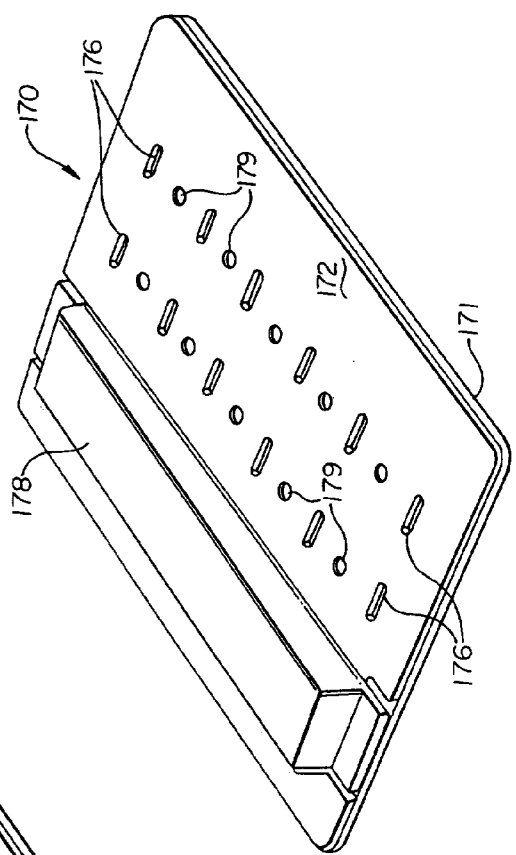
Fig. 27
Fig. 28

US 6,310,961 B1

DISPOSABLE SLEEVE ASSEMBLY FOR SOUND CONTROL DEVICE AND CONTAINER THEREFOR

CROSS REFERENCES TO CO-PENDING APPLICATIONS

This application is a continuation-in-part of U.S. patent application Ser. No. 09/050,203, filed Mar. 30, 1998, entitled "Disposable Foam Sleeve for Sound Control Device and Container There for", to the same assignee as the present application.

FIELD OF THE INVENTION

One aspect of this invention relates to disposable sleeve assemblies for providing contact between the inner surface of a person's ear canal and a sound control device (i.e., a device for wholly, partially, or selectively blocking, transmitting, or amplifying sound such as an ear plug, a stethoscope, and a hearing aid either of the type worn behind the ear or a CIC (completely in the canal) hearing aid, etc.). Another aspect of this invention relates to guards placed at the ends of sound delivery tubes inserted in the ear canal that restrict cerumen from entering those tubes. In yet another aspect, the invention relates to containers for holding unused and used sleeve assemblies and cerumen guards.

BACKGROUND OF THE INVENTION

U.S. Pat. Nos. 4,880,076 and 5,002,151 both disclose hearing aids that are modified in various ways to accept complementary user-disposable foam sleeve adapted to mount on and fit around a distal end portion of the hearing aid to seal it to the user's ear canal. Although technically feasible, all of these combinations have thus far proved commercially unappealing, both because of their technical complexity and their relatively high cost. U.S. Pat. No. 5,682,020 describes another way of sealing a hearing aid to a user's ear canal, viz., by removably adhering a foam layer to the otherwise canal-contacting periphery of the hearing aid. Although this technique is quite effective, the process of adhering the foam to the proper location requires a degree of manual dexterity sometimes lacking in persons who wear hearing aids. Yet another prior art technique involves permanently adhering a foam ring to the hearing aid, thereby preventing the user from removing and replacing it. In the absence of adhesive, such a ring is likely to slide off and remain in the ear canal when the hearing aid is removed.

Guards for the ends of sound delivery tubes inserted in the ear canal that restrict cerumen from entering those tubes are commercially available. Known cerumen guards of this type are moldings of stiff polymeric material that releasably engage a knob-like end part at the end of the sound delivery tube, and provide passageways through the guard sized and oriented to provide that cerumen restricting function.

SUMMARY OF THE INVENTION

The present invention provides a simple and inexpensive sleeve assembly that is easy to apply to and remove from the distal end portion of a sound control device even by children or those enfeebled by age or infirmity; which sleeve assembly can be adapted to provide circumferential contact with a user's ear canal to control sound delivered to that ear canal at a desired level, to provide a cerumen guard at the end of a sound delivery tube included in the sound control device, or to provide both of those functions.

The sleeve assembly according to the present invention comprises a first layer of flexible material (e.g., sound attenuating, slow recovery foam, closed cell foam, open cell foam, reticulated open cell foam, or non-foamed polymeric material depending on the requirements of the sound control device on which the sleeve assembly is used) having a periphery that can be adapted to make partial or complete contact with or conform to the ear canal of a user into which the sleeve assembly is inserted, or to make little or no contact with that ear canal. A stiff resiliently flexible attachment member (e.g., a uniformly thick disc or a generally C-shaped member) having a through opening is fixed to one surface of the first layer. The first layer of material can have a hole between its first and second surfaces aligned with the opening in the attachment member or can be readily penetrable adjacent the opening in the attachment member to afford movement of a knob-like part at the distal end portion of a sound control device through the first layer and the opening in the attachment member, or alternatively, the knob-like part can be moved through the opening in the attachment member from its side opposite the first layer. The knob-like part and the area circumjacent to the opening in the attachment member then cooperate to provide complementary interlocking holding of the sleeve assembly on the end portion of the sound control device. Such interlocking holding will occur if the opening in the attachment member is smaller than the knob-like part so that the area circumjacent to the hole in the attachment member will flex during its passage and will releasably engage the sound control device behind the knob-like part to hold the sleeve assembly on the sound control device. Subsequently, the sleeve assembly can be removed from the sound control device by applying sufficient force to the attachment member to move it back over the knob-like part.

When the distal end of the sound control device is a sound delivery tube that engages the sleeve assembly so that its knob-like part is on the side of the attachment member opposite the first layer, the sleeve assembly can further include a thin layer of sound-transmitting material (e.g., reticulated open cell foam) overlaying the side of the attachment member opposite the first layer of foam that helps prevent detritus or cerumen from the ear canal from entering a sound transmitting passageway through the sound delivery tube. When such a sound delivery tube engages the sleeve assembly so that its knob-like part is on the side of the attachment member adjacent the first layer, the first layer of material can be of such sound-transmitting material so that it will help prevent detritus or cerumen from the ear canal from entering the sound transmitting passageway.

The portion of the human ear canal in which the sleeve assembly is intended to be positioned has an irregular generally oval cross section with dimensions on the order of 5 to 6.5 mm wide by 10 to 13 mm high. Thus, the sleeve assembly, which is accordingly quite small, could be difficult for some persons either to install on or remove from the sound control device. This problem is simplified by a container for a plurality of the sleeve assemblies. Each sleeve assembly can be positioned in the container with the first layer of material and the attachment member and over a passageway in a bottom wall of the container that has a diameter somewhat less than the outer diameter of the attachment member. To install a sleeve assembly in the container on a sound control device, the knob-like part at the distal end of that sound control device is forced downward through one of the sleeve assemblies so that it flexes and deforms the attachment member sufficiently to move through its opening while the attachment member of that sleeve assembly is supported by a portion of the bottom wall circumjacent to the passageway. The attachment member then releasably engages the sound control device adjacent its knob-like part as that knob-like part moves into the passageway. If a desired degree of engagement has thus been achieved between the sound control device and the sleeve assembly, the sleeve assembly will remain on the sound control device when it is lifted from the container. It is important to have the sleeve assembly securely mounted on the sound control device to avoid the problem of having it become detached and remain in the ear canal when the sound control device is removed. Thus, means are provided in the container to restrict removal of the sleeve assembly with the sound control device if that desired degree of engagement has not been achieved, whereupon the sleeve will slip off the sound control device and remain in the container. That means can be provided, for example, by frictional or friable engagement between sleeve assembly and the container, or by a top plate on the container that has finger like portions normally projecting over the sleeve assemblies that must be deflected to allow their removal.

The container can further include a compartment for used sleeve assemblies accessed through a generally keyhole-like slot in a wall of the container. That slot can include a first portion through which a sleeve assembly on a sound control device can easily be moved into the compartment, and a second portion into which the sound control device can then be transversely moved so that the wall of the compartment will engage the sleeve assembly and cause the attachment member to flex and move over the knob-like part of the sound control device to deposit the sleeve assembly in the compartment when force is applied to pull the sound control device out of the second portion of the slot.

BRIEF DESCRIPTION OF THE DRAWINGS

The present invention will be further described with reference to the accompanying drawings wherein like reference numerals refer to like parts in the several views, and wherein:

FIG. 27 is a top perspective view of a container that can contain a plurality of the sleeve assemblies of FIGS. 10–13 and 19–24;

FIG. 28 is a bottom perspective view of the container of FIG. 27;

DETAILED DESCRIPTION OF THE EMBODIMENTS

Figure 1:
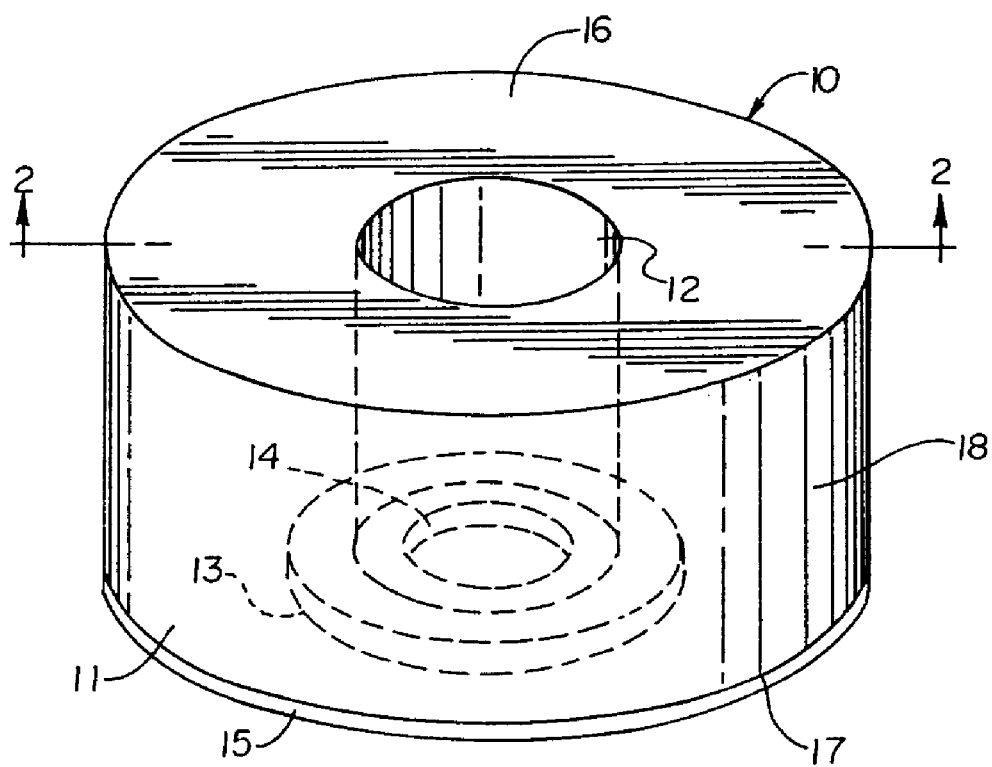
FIG. 1 is an enlarged perspective view of a first embodiment of a sleeve assembly according to the present invention.
Figure 2:
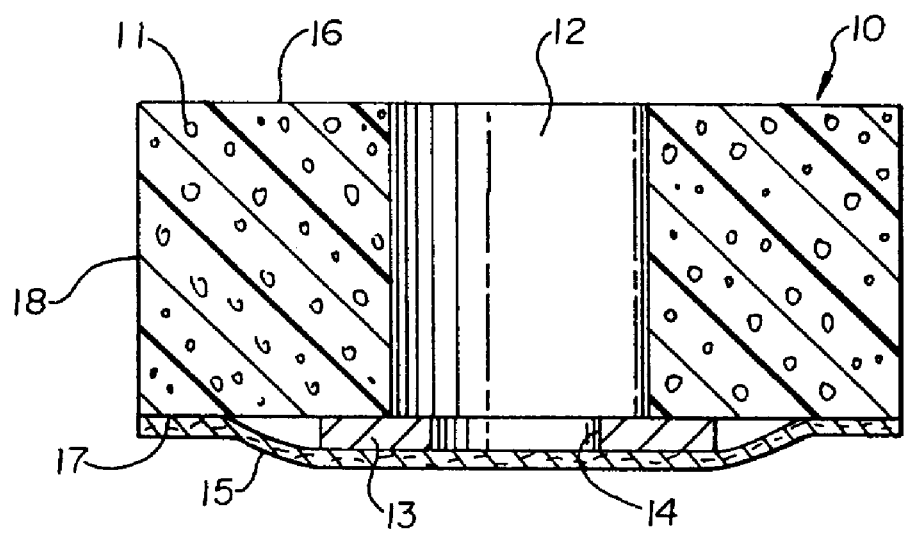
FIG. 2 is a sectional view of the sleeve assembly of FIG. 1, taken approximately along section line 2—2 of FIG. 1 and looking in the direction of the arrows.
Figure 4:
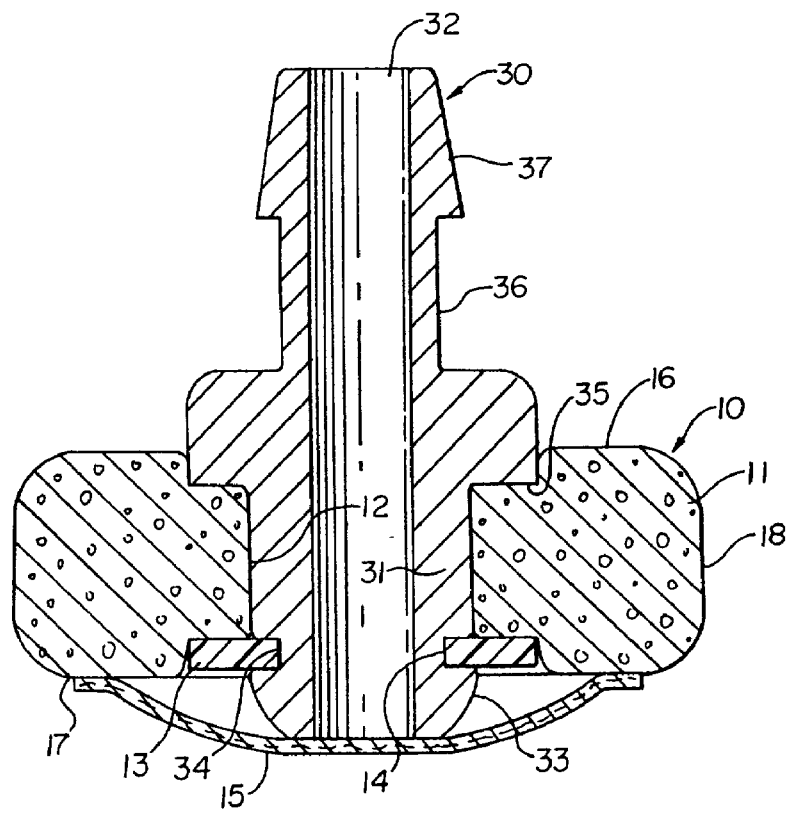
FIG. 4 is a longitudinal-sectional view showing the sleeve assembly of FIGS. 1 and 2 mounted on the sound control device portion of FIG. 3.

Referring now to FIGS. 1, 2 and 4 of the drawings, there is illustrated a first embodiment of a sleeve assembly according to the present invention generally designated by the reference number 10. The sleeve assembly 10 includes a first layer 11 of resilient foam having first and second opposite surfaces 16 and 17, respectively, a cylindrical periphery 18 between those surfaces, and an axial hole 12 extending between those surfaces 16 and 17. On the second surface 17 of the first layer 11 is affixed (e.g., by thermal bonding, adhesive, or mechanical fastening means) a stiff, resiliently deformable attachment member or disc 13 having a through hole or opening 14. The opening 14 is axially aligned with the hole 12 and is about the same size or slightly smaller than the hole 12. Overlaying the side of the disc 13 opposite the first layer 11 and having its periphery attached to the second surface 17 of the first layer 11 is a thin layer 15 of a sound-transmitting material or scrim (e.g., reticulated open cell foam) that helps prevent detritus or cerumen from the ear canal from entering a sound delivery tube of a hearing aid or other sound control device on which sleeve assembly 10 may be mounted (FIG. 4).

Figure 3:
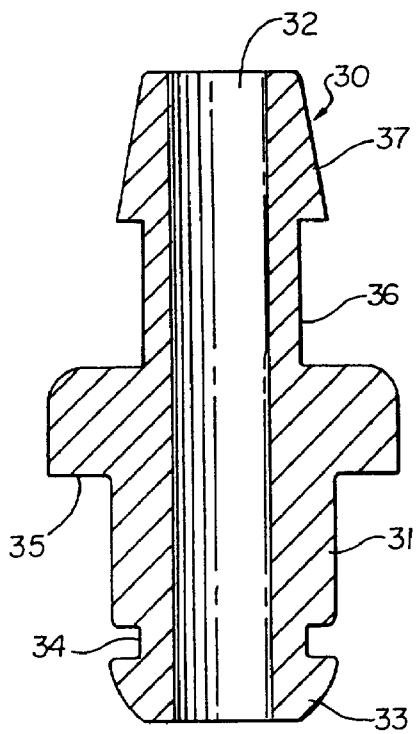
FIG. 3 is a greatly enlarged longitudinal-sectional view of an end portion of a sound control device.

FIG. 3 shows a portion of a sound control device in the form of a sound delivery tube 30 on an ear insertable end portion of which the sleeve of FIGS. 1 and 2 can be mounted, as is illustrated in FIG. 4. The elongate sound delivery tube 30 has a through axially extending sound-transmitting passageway 32, and a knob-like part 33 at one end partially defined by an annular circumferential groove 34 at the proximal end of the knob-like part 33. In use, the knob-like part 33 is inserted through the axial hole 12 in the first layer 11 from its first surface 16 and moved into contact with the portion of the disc 13 surrounding its opening 14. Axial force is then applied so that the portion of the disc 13 circumjacent its opening 14 yields slightly, allowing knob-like part 33 to pass through the opening 14. The circumjacent portion of the disc 13 then springs back so that it seats itself or is retained in the groove 34 to provide a snap fit that securely engages the sleeve assembly 10 on the sound delivery tube 30. As illustrated, the sound delivery tube 30 can be provided with an annular radially outwardly projecting shoulder 35 to insure that the sleeve assembly 10 will be maintained in a fixed location with the first layer 1 slightly compressed after mounting between the disc 13 and the shoulder 35. As is shown in FIG. 4, this compression causes the periphery 18 of the first layer 11 to bulge, thereby restricting contact between the disc 13 and the walls of a user's ear canal. The sound delivery tube 30 also includes a neck 36 at its end opposite the knob-like part 33 that terminates in a fitting or hose barb 37, enabling it to be inserted into and retained within the end of a vinyl tube connected to a sound control device such as a hearing aid of the type worn on or behind the ear. Alternatively, the distal portion of the sound delivery tube fixed to the case of a sound control device, such as a CIC (completely in the canal) hearing aid, can incorporate the parts of the sound delivery tube 30 shown in FIG. 3 that are releasably engaged by the sleeve assembly 10.

The first layer of foam 11 can be of many different types of foam depending on the requirements of the sound control device on which the sleeve assembly 10 is used. For example, for use on a hearing aid the first layer of foam 11 could be of a sound attenuating slow recovery foam, requiring the user to compress the first layer of foam 11 with his fingers before it is placed in the ear canal, after which it recovers its shape sufficiently so that its periphery 18 conforms to the inner surface of the ear canal. Such a first layer 11 of slow recovery foam can then substantially block sounds from entering the ear canal other than through a sound delivery tube on which the sleeve assembly 10 is mounted. Where it is desirable to have sounds enter the ear both through a sound tube on which the sleeve assembly is mounted and through the sleeve assembly (e.g., where the sound tube is connected to a low powered hearing aid or to a telephone head set such as the type used by telemarketers which directs sound into their ear canals without isolating them from their environment), the first layer of foam 11 can be of a more sound transmissive foam such as open cell foam or a reticulated open cell foam selected for the amount of sound transmission desired. Typically, such open cell foams are sufficiently compressible that the periphery 18 will conform to the inner surface of the ear canal as the first layer 11 is pushed into it. As a non-limiting example, the first layer 11 can have a diameter of between 0.37 to 0.63 inch or 1 to 1.6 cm, an axial length between its surfaces 16 and 17 of between 0.2 to 0.6 inch or 0.5 to 1.5 cm, and a hole 12 diameter of about 0.08 inch or 0.2 cm. The resiliently deformable disc 13 can be of a polymeric material such as 0.01 to 0.02 inch or 0.02 to 0.05 cm thick polyurethane, PET, or polyethylene. The disc 13 can have an outer diameter of 0.19 to 0.26 inch or 0.48 to 0.66 cm and an opening 14 diameter of about 0.1 inch or 0.25 cm. The diameter of the opening 14 can provide from a clearance fit of about 0.005 inch or 0.013 cm to an interference fit of about 0.020 inch or 0.051 cm between the disc 13 and the bottom of the groove 34 on the sound delivery tube 30 or other portion of a sound control device it is adapted to engage, that fit being selected to provide the degree of engagement desired between the sleeve assembly 10 and the sound control device. Such interference fits will cause a portion of the disc 13 to remain in a slightly frusta-conical shape after engagement around the sound delivery tube 30, which insures firm engagement therebetween.

A currently preferred open cell reticulated foam for use as the layer 15 of sound-transmitting cerumen restricting material and as the other layers of sound-transmitting cerumen restricting open cell reticulated foam described below with reference to the other embodiments is a polyester urethane foam about 0.05 inch or 0.13 centimeter thick, having about 100 pores per lineal inch or 40 pores per lineal centimeter and a void volume of about 97 percent. Somewhat greater thicknesses may be appropriate for some individuals and uses. This foam is also oleophilic, which is considered advantageous for use as a cerumen guard. Foams meeting these criteria are obtained from Foamex under the trade designation "SIF Filter Foam".

Figure 5:
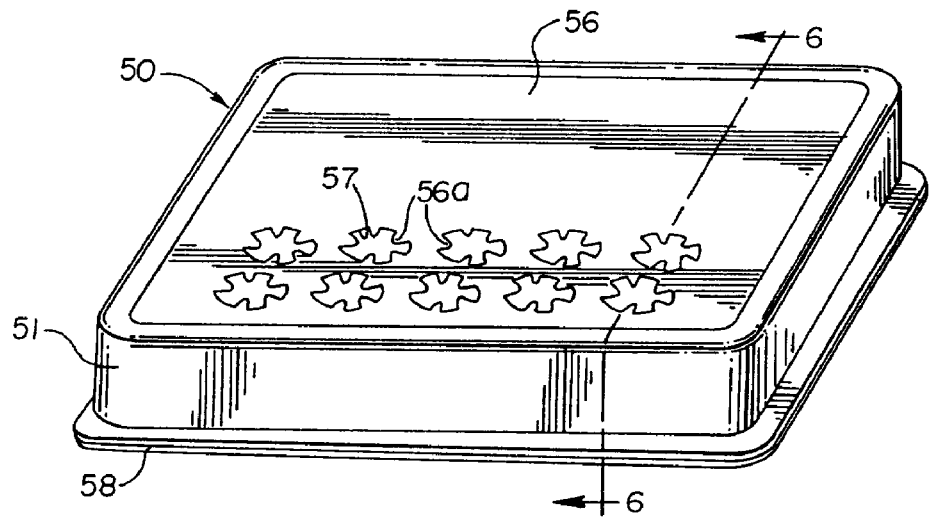
FIG. 5 is a perspective view of a container that can contain a plurality of the sleeve assemblies of FIGS. 1 and 2.
Figure 6:
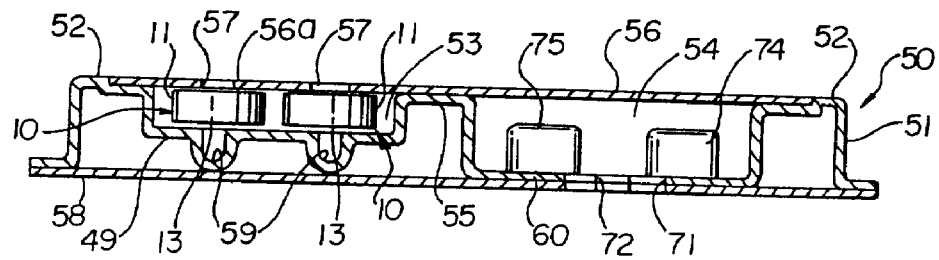
FIG. 6 is a sectional view of the container of FIG. 5 in which are positioned a plurality of the sleeve assemblies of FIGS. 1 and 2, the sectional view being taken approximately along section line 6—6 of FIG. 5 looking in the direction of the arrows.

FIGS. 5 and 6 illustrate a tray-like container 50 in which a plurality of the sleeve assemblies 10 can be contained. A main portion 51 of the container 50, which can be vacuum formed (e.g., from a 0.025 inch or 0.64 cm thick sheet of vinyl), forms a vertical side wall 48 on four sides of the container 50 and has, inboard of that side wall 48, two recessed portions separated by a transverse wall 55 that define a first compartment 53 adapted to receive unused sleeve assemblies 10, and a second compartment 54 adapted to receive used sleeve assemblies 10. Attached to a peripheral ledge 52 adjacent the top of the side wall 48 and to the transverse wall 55 is a planar upper plate 56 (e.g., of 0.024 SBB blister board) which has a plurality of holes 57. The holes 57 are defined in part by radially inward extending finger like portions 56a of the upper plate 56. The distal ends of the finger like portions 56a define central portions of the holes 57 that have diameters slightly less than the maximum outer diameters of the sleeve assemblies 10. The main portion 51 of the container 50 includes a part providing a floor 49 for the compartment 53 that includes downwardly protruding portions forming passageways or depressions 59 that are directly below the holes 57. The diameters of the depressions 59 are somewhat less than the outer diameter of the discs 13, but somewhat greater than the diameter of the knob-like part 33 of the sound delivery tube 30. To withdraw a sleeve assembly 10 from the compartment 53, the user inserts the knob-like part 33 of the sound delivery tube 30 (or a similarly shaped distal end portion of another sound control device) through one of the holes 57 in the upper plate 56 and then through the axial hole 12 in the sleeve assembly 10 below that hole 57. The knob-like part 33 is then pressed through the opening 14 in the disc 13 which is supported by part of the floor 49 circumjacent to the depression 59 below that sleeve assembly 10, and moves into that depression 59. The portion of the disc 13 circumjacent the hole 14 resiliently deforms as the knob-like part 33 passes through it, and then contracts and becomes seated or retained in the groove 34 of the sound delivery tube 30. Removal of the sound delivery tube 30 through the hole 57 in the plate 56 also removes the sleeve 10, which is now mounted on the sound delivery tube 30. Effective mounting occurs when the retaining force caused by the positioning of the disc 13 in the groove 34 is greater than the restraining force caused by deflecting the finger like portions 56a to expand the hole 57 sufficiently for passage of the first layer 11 which defines the maximum outer diameter for the sleeve assembly 10. If for some reason, sufficient engagement has not been achieved between the disc 13 and the sound delivery tube 30, the distal portions of the finger like portions 56a will pull the sleeve assembly 10 off of the sound delivery tube 30 as the sound delivery tube 30 is pulled from the container 50. This will occur because the diameter of the first layer 11 of the sleeve assembly 10 exceeds the diameter of the central portion of the hole 57 defined by the distal ends of the finger like portions 56a and is restrained because sound delivery tube 30 cannot apply sufficient force to cause the finger like portions 56a to flex enough to allow the first layer 11 of the sleeve assembly 10 to pass through the hole 57.

Figure 8:
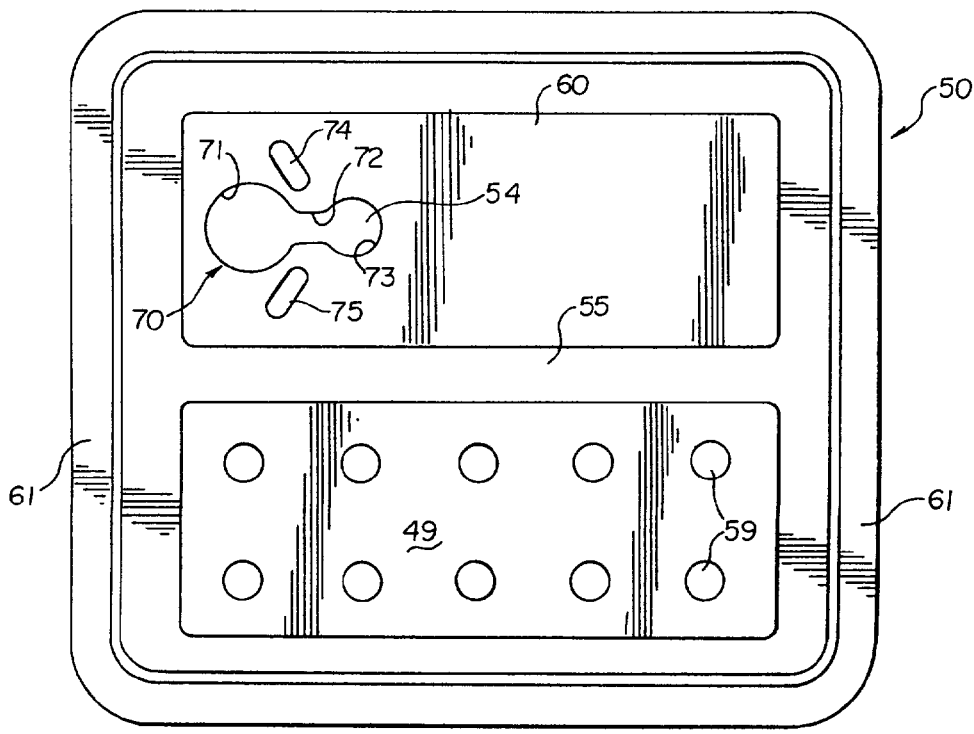
FIG. 8 is a bottom plan view of the container of FIG. 5 with a bottom plate of the container removed to show details.

The second compartment 54 adapted to receive used sleeve assemblies 10 is best seen in FIGS. 6 and 8. The container 50 includes a bottom plate 58 (e.g., also of 0.024 SBB blister board) attached to a flange 61 around the bottom edge of the side wall 48 and to part of the main portion 51 forming a bottom 60 of the compartment 54. The bottom plate 58 and the bottom 60 of the compartment 54 have a through generally keyhole shaped slot 70 to provide means for removing used sleeve assemblies 10 from sound control devices such as the sound delivery tube 30 and automatically storing them in the compartment 54. The keyhole slot 70 includes a major circular portion 71, a rectangular portion 72, and minor circular portion 73. The diameter of the major circular portion 71 is slightly greater than the diameter of the first layer 11 of the sleeve assembly 10; the width of the rectangular portion 72 is less than the diameter of the first layer 11 and of the shoulder 35, but greater than the diameter of the neck 36; and the diameter of the minor circular portion 73 is noticeably less than the diameter of the sleeve assembly 10, but slightly greater than the diameter of the shoulder 35. To remove a sleeve assembly 10 from a sound control device such as the sound delivery tube 30 on which the sleeve assembly 10 is mounted, the sleeve assembly 10 on the sound delivery tube 30 is inserted through the major circular portion 71, whereupon the neck 36 is slid transversely along the rectangular portion 72 to the smaller circular portion hole 73. The sound delivery tube 30 is then pulled away from the bottom 60 and bottom plate 58, the resultant force causing the portion of the disc 13 circumjacent the hole 14 to spring away and allow the sleeve assembly 10 to be pulled off of the sound delivery tube 30 and deposited in the compartment 54. Portions 74 and 75 of the bottom 60 project into the compartment 54 and are spaced and angled to slightly compress the first layer 11 of the sleeve assembly 10 as it is slid toward minor circular portion 73 and to thereafter restrict movement of that and other used sleeve assemblies 10 in the compartment 54 toward the major circular portion 71 of the slot 70.

Figure 9:
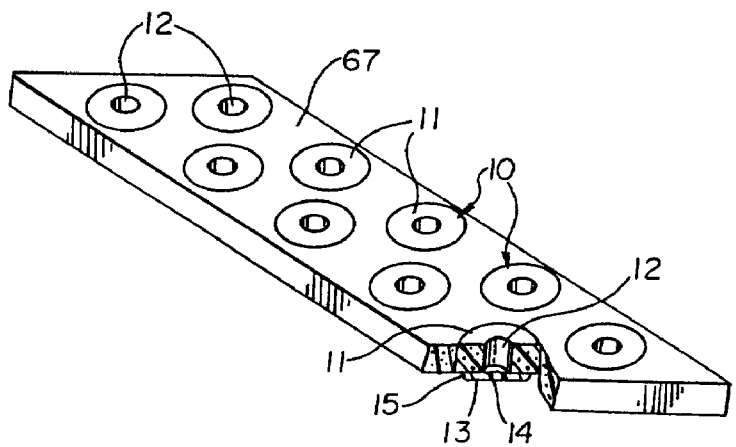
FIG. 9 is a perspective view of a block of foam from which sleeve assemblies of the type shown in FIG. 1 have been die-cut but not physically removed from the surrounding "weed" which can advantageously be used in the container of FIG. 5, certain parts having been broken away to show details.
Figure 7:
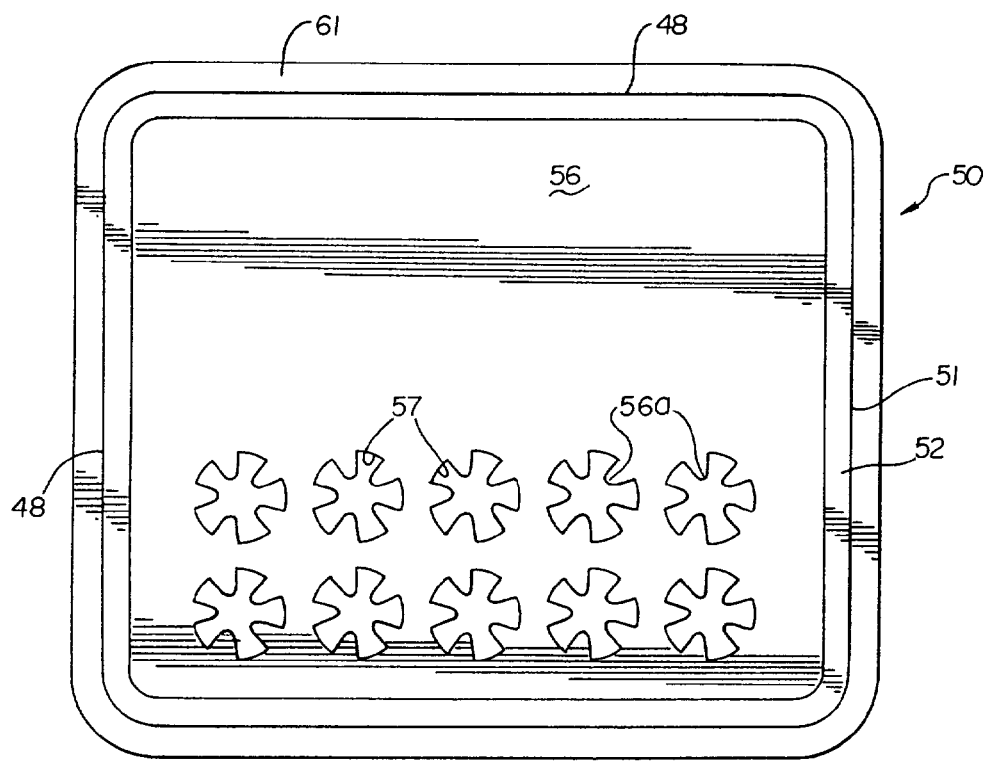
FIG. 7 is an upper plan view of the container of FIG. 5.

FIG. 9 illustrates a convenient way of positioning a plurality of sleeve assemblies in the tray-like container 50 of FIGS. 5–8. A rectangular foam slab 67 corresponding in shape to the compartment 53 and having a series of discs 13 affixed to its lower surface, is die-cut to delineate individual sleeve assemblies 10 without physically removing them from the surrounding "weed". The foam slab 67 is positioned in the compartment 53 to hold and position the sleeve assemblies it delineates in the proper position between the holes 57 and the depressions 59.

If desired, container 50 may be provided with a lid, shrink wrapped or packaged in a cardboard sleeve.

Those skilled in the art, having read the foregoing disclosure, will be able to make numerous modifications and applications without departing from the spirit of the invention. For example, the first layer 11 may have other than a cylindrical periphery such as an oval or contoured periphery more closely approximating the shape of the human ear canal. In such event, the disc 13, the hole 14, the knob-like part 33 and the groove 34 could likewise be oval or otherwise shaped to help provide self-orientation of the sound control device. For some purposes it may be desirable for the periphery of the first layer 11 to have the shape of a truncated cone. The periphery of the first layer 11 could define generally axially aligned flutes to provide channels through which low frequency sounds can escape from the ear canal. Alternatively, providing bores between the first and second surfaces of the first layer 11 could provide such channels. Other modifications of the first layer 11 could be appropriate for hearing aids designed to amplify or depress certain frequencies, as in hearing aids for reducing the sound of muzzle blasts in rifle or shotgun shooting while amplifying sounds that can improve safety and accuracy, or for other specialized hearing aids such as those that can amplify the high frequencies of sounds made by birds and wildlife. To make the opening 14 in the disc 13 more easily penetrated by the knob-like part at the distal end of a sound control device, the disc 13 may be provided with radially extending slits. Attachment members other than a disc 13 may be used, such as a uniformly thick generally C-shaped attachment member having generally the same shape as commercially available external snap rings. Such an attachment member has a discontinuous periphery and can resiliently deform to allow portions of it to spread apart to afford passage of the knob-like part 33 through its opening, rather than have an annular portion around its opening deform to afford passage of the knob-like part 33 as occurs with the disc 13. It may be possible to deposit a layer of stiff resilient polymeric material on a surface of the first layer to form the attachment member. A variety of other complementary locking systems could also be used to attach the sleeve 10 to a sound control device; for example, the knob-like part on the distal end of the sound control device might have a rectangular cross-section, with the opening 14 in the disc 13 being correspondingly rectangular, so that after inserting the distal end portion of the sound control device through the opening 14, a quarter turn would provide an effective interlocking means between the knob-like part and the area circumjacent to the opening in the disc to hold the sleeve assembly on the sound control device. Other interlocking means or arrangements can readily be envisioned. Where first layers of greater axial length are desired, more than one first layer of foam may be mounted on the sound control device in which event only the first layer of foam at the distal end of the sound control device will be provided with a disc to provide the locking means. Such a structure is described below with reference to FIG. 31.

Figure 10:
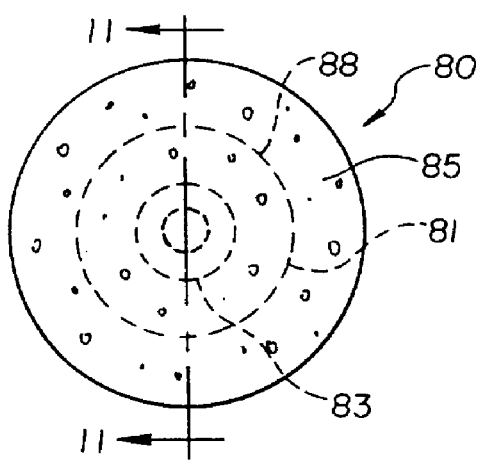
FIG. 10 is an enlarged end view of a second embodiment of a sleeve assembly according to the present invention.
Figure 11:
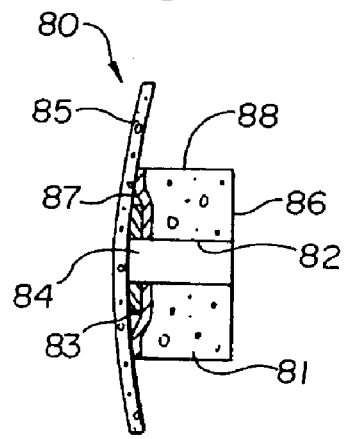
FIG. 11 is a sectional view of the sleeve assembly of FIG. 10, taken approximately along section line 11—11 of FIG. 10 and looking in the direction of the arrows.

FIGS. 10 and 11 of the drawings illustrate a second embodiment of a sleeve assembly 80 according to the present invention that can be attached to a sound control device such as by the end portion of the sound delivery tube 30 described above in the same manner as the sleeve assembly 10. The sleeve assembly 80 includes a first layer 81 of foam having first and second opposite surfaces 86 and 87, respectively, a cylindrical periphery 88 between those surfaces, and having an axial hole 82 extending between those surfaces 86 and 87. The foam in the first layer 81 could be of sound attenuating slow recovery foam, of a closed cell foam, of an open cell foam, or of a reticulated open cell foam, depending on the requirements of the sound control device on which the sleeve assembly 80 is used. On the second surface 87 of the first layer 81 is affixed (e.g., by thermal bonding, adhesive, or mechanical fastening means) a stiff, resiliently deformable attachment member or disc 83 having a through hole or opening 84 which could be similar to or the same as the disc 13 described above. The opening 84 is axially aligned with the hole 82 and is about the same size or slightly smaller than the hole 82. Overlaying the side of the disc 83 opposite the first layer 81 and having its adjacent side attached to the second surface 87 of the first layer 81 (e.g., attached by adhesive or by heat sealing using a layer of polyethylene tape therebetween) is a thin layer 85 of sound-transmitting material such as open cell reticulated foam. The layer 85 of sound-transmitting material helps prevent detritus or cerumen from the ear canal from entering the sound delivery tube of a hearing aid or other sound control device on which sleeve assembly 80 may be mounted in the manner illustrated and described above with reference to FIG. 4. The periphery of the layer 85 of sound transmitting material extends beyond the periphery 88 of the first layer 81 so that it will extend from the second surface 87 and along the periphery 88 of the first layer 81 as the sleeve assembly 80 is inserted into the ear canal to cover and soften the leading edge of the first layer 81 of foam, and can thereafter engage the inner surface of the ear canal along the periphery 88 of the first layer 81 to help hold the sleeve assembly 80 in the ear canal.

Figure 12:
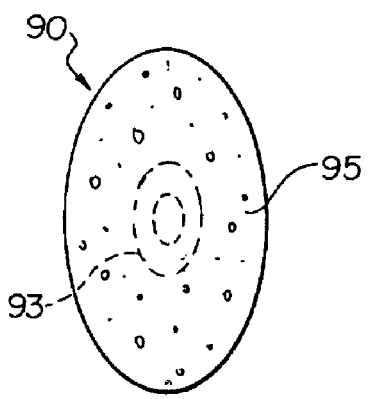
FIG. 12 is an enlarged end view of a third embodiment of a sleeve assembly according to the present invention.
Figure 13:
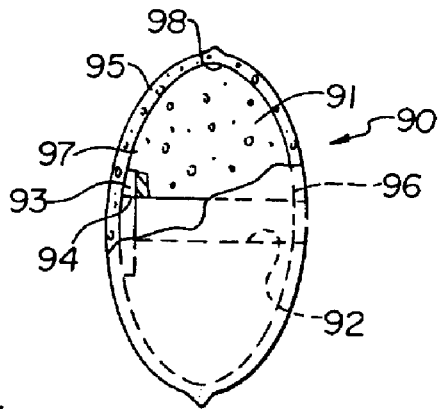
FIG. 13 is a side view of the sleeve assembly of FIG. 12 in which parts are broken away and sectioned to show details.

FIGS. 12 and 13 of the drawings illustrate a third embodiment of a sleeve assembly 90 according to the present invention that can be attached to a sound control device such as by the end portion of the sound delivery tube 30 described above in the same manner as the sleeve assembly 10. The sleeve assembly 90 includes a first layer 91 of foam having first and second opposite surfaces 96 and 97, respectively, an arcuate periphery 98 between those surfaces, and having an axial hole 92 extending between those surfaces 96 and 97. The foam in the first layer 91 could be of sound attenuating slow recovery foam, of a closed cell foam, of an open cell foam, or of a reticulated open cell foam, depending on the requirements of the sound control device on which the sleeve assembly 90 is used. On the second surface 97 of the first layer 91 is affixed (e.g., by thermal bonding, adhesive, or mechanical fastening means) a stiff, resiliently deformable attachment member or disc 93 having a through hole or opening 94 which could be similar to or the same as the disc 13 described above. The opening 94 is axially aligned with the hole 92 and is about the same size or slightly smaller than the hole 92. Enveloping the side of the disc 93 opposite the first layer 91, both surfaces 96 and 97 of the first layer 91 and its periphery 98 is a thin layer 95 of sound-transmitting material (e.g., a layer of open cell reticulated foam) which can be applied as two layers heat sealed or adhered together around the periphery 98 of the first layer 91. The layer 95 of sound transmitting material helps prevent detritus or cerumen from the ear canal from entering the sound delivery tube of a hearing aid or other sound control device on which sleeve assembly 90 may be mounted in the manner illustrated and described above with reference to FIG. 4. The material of the outer layer 95 of sound transmitting material can be selected to provide a desired feel of the sleeve assembly 90 against the inner surface of the ear canal and/or a desired appearance for the sleeve assembly 90. Also, heat sealing together two layers of sound transmitting material around the first layer 91 and the disc 93 to form the layer 95 could facilitate manufacturing of the sleeve assembly 90.

Figure 14:
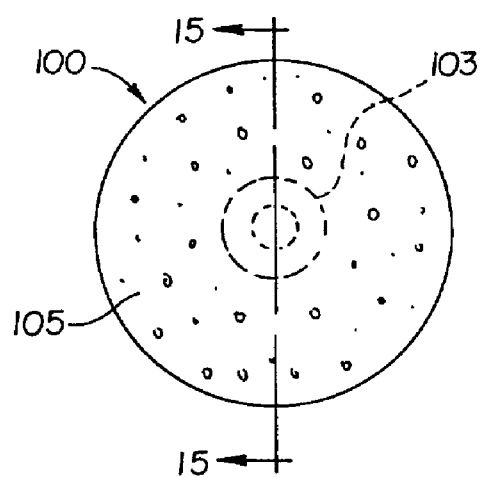
FIG. 14 is an enlarged end view of a fourth embodiment of a sleeve assembly according to the present invention.
Figure 15:
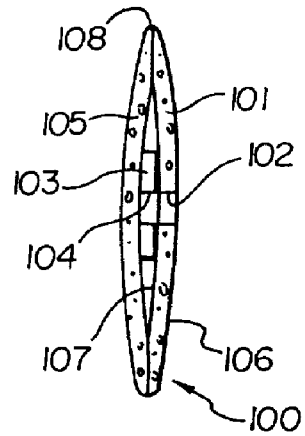
FIG. 15 is a sectional view of the sleeve assembly of FIG. 14, taken approximately along section line 15—15 of FIG. 14 and looking in the direction of the arrows.

FIGS. 14 and 15 of the drawings illustrate a fourth embodiment of a sleeve assembly 100 according to the present invention that can be attached to a sound control device such as by the end portion of the sound delivery tube 30 described above in the same manner as the sleeve assembly 10, or to an ear insertable end portion 110 of a sound control device as is described below with reference to FIG. 16. The sleeve assembly 100 includes a thin disc-like first layer 101 of resiliently flexible polymeric or other suitable material (e.g., of 0.018 inch or 0.046 centimeter thick high density polyethylene) having first and second opposite surfaces 106 and 107, respectively, a cylindrical periphery 108, and an axial hole 102 extending between those surfaces 106 and 107. The polymeric material in the first layer 101 could be of an extruded or otherwise formed polymeric material such as that noted above, of a closed cell foam, of an open cell foam, or of a reticulated open cell foam, depending on the requirements of the sound control device on which the sleeve assembly 100 is used. On the second surface 107 of the first layer 101 is affixed (e.g., by thermal bonding, adhesive, or mechanical fastening means) a stiff, resiliently deformable attachment member or disc 103 having a through hole or opening 104 which could be similar to or the same as the disc 13 described above. The opening 104 is axially aligned with the hole 102 and is about the same size as the hole 102. Over the side of the disc 103 opposite the first layer 101 and along outer portions of the second surface 107 of the first layer 101 is a thin disc-like layer 105 of sound-transmitting material such as an open cell reticulated foam which has the same diameter as the first layer 101 and has its periphery attached (e.g., by thermal bonding, adhesive, or heat sealing) to the periphery 108 of the first layer 101. The peripheries of the layers 101 and 105 could be oval rather than circular as illustrated. The layer 105 of sound transmitting material helps prevent detritus or cerumen from the ear canal from entering the sound delivery tube of a hearing aid or other sound control device on which sleeve assembly 100 may be mounted. The portions of the first and outer layers 101 and 105 that extend beyond the disc 103 have a sufficient outer diameter (e.g., an outer diameter in the range of about 0.6 to 0.7 inch or 16 to 18 millimeter) and are sufficiently flexible that they will bend and assume a generally umbrella-like shape conforming to the generally oval inner surface of an ear canal into which the sleeve assembly 100 is inserted in an end portion of a sound control device such as the end portion 110 of FIG. 16. A part of the outer layer 105 adjacent its periphery will then be pressed against the inner surface of the ear canal by the resilience of the layers 101 and 105. Upon subsequent removal of the end portion 110 from the ear canal, the portions of the first and outer layers 101 and 105 adjacent the disc 103 will move past that part of the outer layer 105 pressed against the ear canal, thereby inverting the portions of the first and outer layers 101 and 105 that extend beyond the disc 103 as the sleeve assembly 100 moves out of the ear canal with the end portion 110.

The sleeve assembly 100 could be modified to provide a cerumen guard that primarily only prevents detritus or ccrumen from the ear canal from entering the sound delivery tube of a hearing aid or other sound control device on which sleeve assembly 100 may be mounted. This could be done by reducing the diameters of the first and outer layers 101 and 105 so that they are about the same as, or only slightly larger than, the outer diameter of the disc 103 (e.g., 0.19 to 0.26 inch or 4.8 to 6.6 millimeter), in which event their peripheries will not make extensive contact with the inner surfaces of normal adult ear canals which vary considerably in size, but are typically in the range of about 10 to 13 mm high and 5 to 6.5 mm wide between the first and second bends in the ear canal where the sleeve assembly 100 is intended to be positioned.

Figure 16:
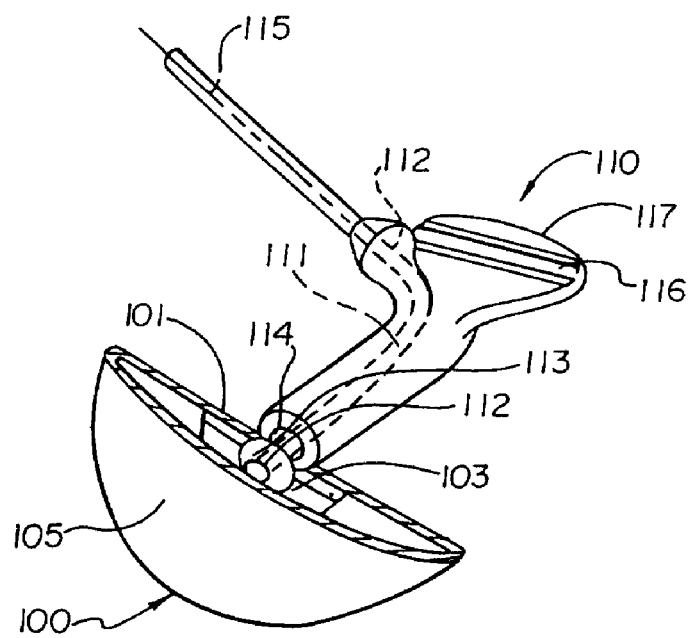
FIG. 16 is a perspective view of an end portion of a sound control device to which is attached the sleeve assembly of FIGS. 14 and 15, a portion of which sleeve assembly has been broken away to show details.

FIG. 16 shows an ear insertable end portion 110 of a sound control device on which any one of the sleeve assemblies described in this application can be mounted, but which will be described with reference to use with the sleeve assembly 100 illustrated in FIGS. 14, 15 and 16. The generally L-shaped end portion 110 of a sound control device includes a first elongate portion 111 having a knob-like part 113 at one end partially defined by an annular circumferential groove 114 at the proximal end of the knob-like part 113, and a second portion 112 extending at about a right angle from the end of the first portion 111 opposite the knob-like part 113. The portion 110 has a sound-transmitting passageway 112 extending axially through both of the portions 111 and 112 that opens through the center of the knob-like part 113. Sound can be fed into the end of the passageway 112 opposite the knob-like part 113 through a micro-tube 115 from a sound producing, transmitting or amplifying portion of a sound control device (not shown) such as a floppy disc player, or a healing aid of the type worn on the ear, such as the "hearing enhancer" made by ReSound, Redwood City, CA. The portion 110 of the sound control device can be engaged with the sleeve assembly 100 by inserting the knob-like part 113 through the axial hole 102 in the first layer 101 from its first surface 106 and moving it into contact with the portion of the disc 103 surrounding its opening 104. Axial force is then applied so that the portion of the disc 103 circumjacent its opening 104 yields slightly, allowing knob-like part 113 to pass through the opening 104. The circumjacent portion of the disc 103 then springs back so that it scats itself or is retained in the groove 114 to provide a snap fit that securely engages the sleeve assembly 100 on the portion 110 of the sound control device. The sleeve assembly 100 on the portion 110 of the sound control device can then be manually positioned at a position past the first bend in a person's ear canal by grasping a flatted generally triangular tab-like part 116 of the portion 110 spaced along the elongate part 111 from the knob-like part 113 and inserting the distal end of the first elongate portion 111 carrying the sleeve assembly 100 into the ear canal. As it moves into that position in the ear canal, the periphery of the sleeve assembly 100 will conform to and rest against the irregular but generally oval inner surface of the ear canal as described above. That position of the sleeve assembly 100 in the ear canal will be signaled to the user by alignment of an edge 117 on the side of the tab-like part 116 opposite the knob-like part 113 with the projecting tragus at the inlet to the ear canal, which tragus will thereafter partially hide the portion 110 of the sound control device from view. The distance between the edge 117 on the tab-like portion 116 and the groove 114 is in the range of about 0.5 to 1 inch or 1.3 to 2.5 centimeters, which, for most adult persons, will place the sleeve assembly 100 between the first and second bends in a person's ear canal when the edge 117 is aligned with that person's tragus.

Figure 17:
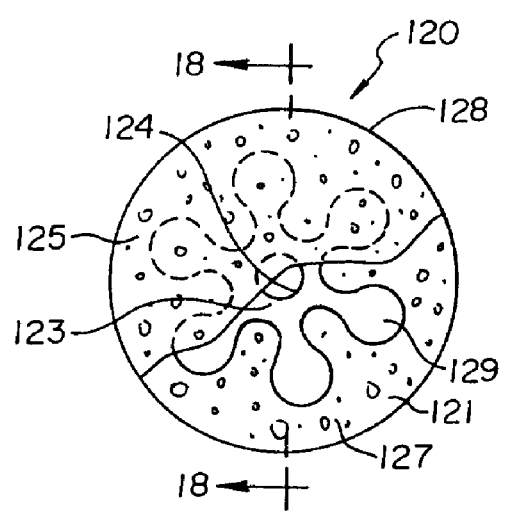
FIG. 17 is an enlarged end view of a fifth embodiment of a sleeve assembly according to the present invention in which a part is broken away to show details.
Figure 18:
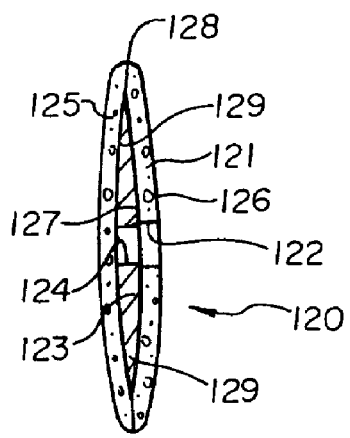
FIG. 18 is a sectional view of the sleeve assembly of FIG. 17, taken approximately along section line 18—18 of FIG. 17 and looking in the direction of the arrows.

FIGS. 17 and 18 of the drawings illustrate a fifth embodiment of a sleeve assembly 120 according to the present invention that can be attached to a sound control device such as by the end portion 110 described above in the same manner as the sleeve assembly 100. The sleeve assembly 120 includes a thin disc-like flexible first layer 121 of polymeric or other suitable material having first and second opposite surfaces 126 and 127, respectively, a cylindrical periphery 128, and an axial hole 122 extending between those surfaces 126 and 127. The material in the first layer 121, for example, could be any of the materials noted above for the first layer 101, depending on the requirements of the sound control device on which the sleeve assembly 120 is used. On the second surface 127 of the first layer 121 is affixed (e.g., by thermal bonding, adhesive, or mechanical fastening means) a stiff, resiliently deformable attachment member or disc 123 having a through hole or opening 124, which disc 123 could have similar or the same material, thickness, and hole 124 diameter properties as the disc 13 described above, but differs from that disc 13 in that it has a larger outer diameter defined by lobe-like portions 129 of the disc 123 radially projecting from a circular central portion thereof. The opening 124 is axially aligned with and is about the same size as the hole 122. Over the side of the disc 123 opposite the first layer 121 and along outer portions of the second surface 127 of the first layer 121 is a thin circular layer 125 of sound-transmitting material such as an open cell reticulated foam which has the same diameter as the first layer 121 and has its periphery attached (e.g., by thermal bonding, adhesive, or heat sealing) to the periphery 128 of the first layer 121. The layer 125 of sound transmitting material helps prevent detritus or cerumen from the ear canal from entering a sound delivery tube of a sound control device on which sleeve assembly 120 may be mounted. The peripheral portions of the first layer 121 and outer layer 125 receive partial support from the lobe-like portions 129 of the disc 123 which can be advantageous to help those peripheral portions conform closely to the inner surface of an ear canal in which the sleeve assembly 120 is positioned as by the end portion 110.

The peripheries of the layers 121 and 125 could be oval rather than circular as illustrated, and the lobe-like portions 129 of the disc 123 could extend different distances to conform with such an oval periphery for the sleeve assembly 120. If the fit of the disc 123 on a sound control device is adapted so that the sleeve assembly 120 can rotate above the end portion of that sound control device, conceivably such a supported oval periphery could cause the sleeve assembly 120 to align itself with the generally oval cross section of an ear canal into which it is inserted.

Figure 19:
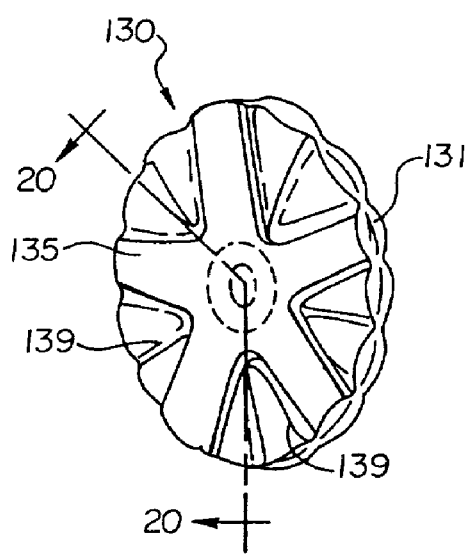
FIG. 19 is a perspective view of a sixth embodiment of a sleeve assembly according to the present invention.
Figure 20:
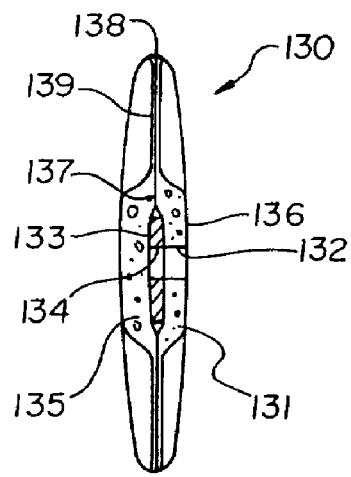
FIG. 20 is a sectional view of the sleeve assembly of FIG. 19, taken approximately along section line 20—20 of FIG. 19 and looking in the direction of the arrows.

FIGS. 19 and 20 of the drawings illustrate a sixth embodiment of a sleeve assembly according to the present invention generally designated by the reference numeral 130 that can be attached to a sound control device such as by the end portion 110 described above in the same manner as the sleeve assembly 100. The sleeve assembly 130 includes a thin disc-like first layer 131 of polymeric or other suitable material having first and second opposite surfaces 136 and 137, respectively, a cylindrical periphery 138, and an axial hole 132 extending between those surfaces 136 and 137. The material of the first layer 131 could, for example, be of any of the materials noted above for the first layer 101, depending on the requirements of the sound control device on which the sleeve assembly 130 is used. On the second surface 137 of the first layer 131 is affixed (e.g., by thermal bonding, adhesive, or mechanical fastening means) a stiff, resiliently deformable attachment member or disc 133 having a through hole or opening 134 which could be similar to or the same as the disc 13 described above. The opening 134 is axially aligned with the hole 132 and is about the same size or slightly smaller than the hole 132. Over the side of the disc 133 opposite the first layer 131 and along outer portions of the second surface 137 of the first layer 131 is a thin circular layer 135 of sound-transmitting material such as open cell foam which has the same diameter as the first layer 131. The first layer 131 and the layer 135 are attached (e.g., by adhesive or heat sealing) around the periphery of the disc 133 by radially outwardly extending sealing lines 139. The layer 135 of open cell foam helps prevent detritus or cerumen from the ear canal from entering the sound delivery tube of a sound control device on which sleeve assembly 130 may be mounted. The radially extending sealing lines 139 stiffen the foam first layer 131 and outer layer 135 and form radially extending flutes around the disc 133 that can be advantageous to help those peripheral portions conform to and press against the inner surface of an ear canal in which the sleeve assembly 130 is positioned as by the end portion 110.

Figure 21:
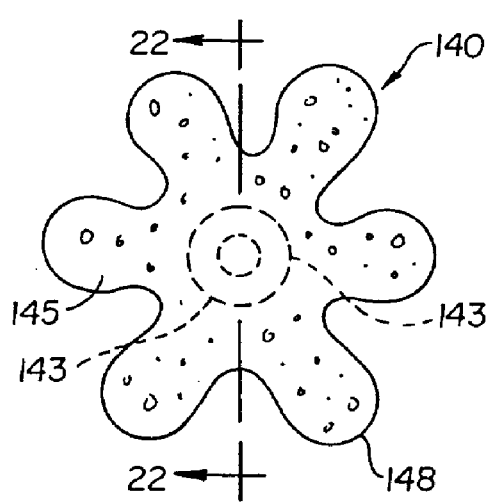
FIG. 21 is an enlarged end view of a seventh embodiment of a sleeve assembly according to the present invention.
Figure 22:
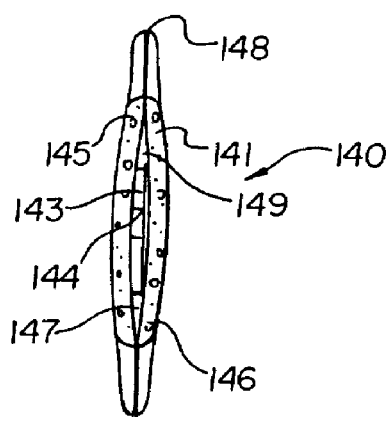
FIG. 22 is a sectional view of the sleeve assembly of FIG. 21, taken approximately along section line 22—22 of FIG. 21 and looking in the direction of the arrows.

FIGS. 21 and 22 of the drawings illustrate a seventh embodiment of a sleeve assembly 140 that illustrates three additional features that can be incorporated in a sleeve assembly according to the present invention. The sleeve assembly 140 includes a thin disc-like first layer 141 of polymeric or other suitable material having first and second opposite surfaces 146 and 147, respectively, and a generally oval periphery 148 defined by spaced projecting lobes. The foam in the first layer 141 could, for example, be of any of the materials described above for the first layer 101, depending on the requirements of the sound control device on which the sleeve assembly 140 is used. On the second surface 147 of the first layer 141 is affixed (e.g., by thermal bonding, adhesive, or mechanical fastening means) a stiff, resiliently deformable attachment member or disc 143 having a through hole or opening 144 which could be similar to or the same as the disc 13 described above. The first layer of foam 141 extends across the opening 144. Over the side of the disc 143 opposite the first layer 141 and along outer portions of the second surface 147 of the first layer 141 is a thin layer 145 of sound-transmitting material such as open cell reticulated foam which helps prevent detritus or cerumen from the ear canal from entering a sound delivery tube or other sound control device on which sleeve assembly 140 may be mounted, and which has the same diameter and peripheral shape as the first layer 141. The layers 141 and 145 are attached together (e.g., by adhesive or heating sealing) around their peripheries. Between the layers 141 and 145 and extending radially outwardly from the hole 144 is a layer 149 of water absorbent or adsorbent material such as that commercially available as Grade X1040 DRITEX from Fort James, Green Bay, Wis. The first layer 141 is sufficiently thin that it can be pierced by or can be stretched around the knob-like part 113 on the end portion 110 of a sound control device as the end portion 110 is pressed through the first layer 141 and through the opening 144 in the disc 143 to engage the sleeve assembly 140 with the sound control device. The projecting lobes defining the generally oval periphery 148 of the sleeve assembly 140 can help to conform the peripheral portions of the layers 141 and 142 to the inner surface of an ear canal in which the sleeve assembly 140 is positioned. The layer of material 149 will absorb or adsorb moisture in an ear canal in which the sleeve assembly 140 is positioned which can prevent that moisture from clogging a sound tube leading to the ear canal. Heretofore, moisture from the ear canal has often caused problems by clogging sound tubes leading to the ear canal, such as the often used 0.076 inch or 0.193 I.D. no. 13 TYGON sound tube. Such moisture would cause a particular problem by clogging a micro sound tube (e.g., a 0.015 inch or 0.381 centimeter I.D. tube) leading to the ear canal due to capillary action.

Figure 23:
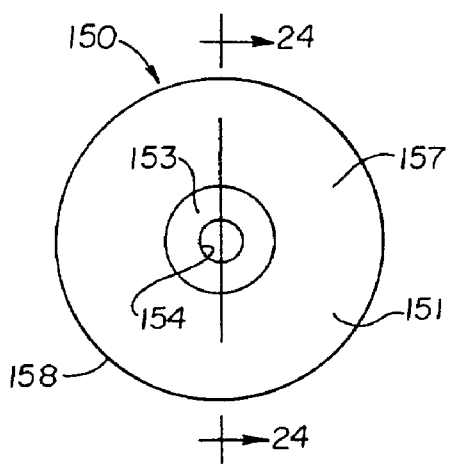
FIG. 23 is an enlarged end view of an eighth embodiment of a sleeve assembly according to the present invention.
Figure 24:
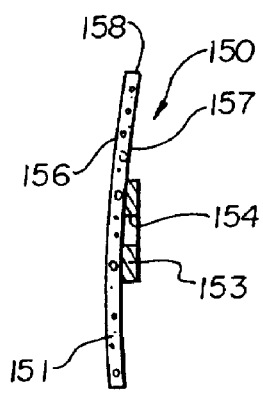
FIG. 24 is a sectional view of the sleeve assembly of FIG. 23, taken approximately along section line 24—24 of FIG. 23 and looking in the direction of the arrows.

FIGS. 23 and 24 illustrate an eighth embodiment of a sleeve assembly 150 according to the present invention. The sleeve assembly 150 includes a thin disc-like first layer 151 of a sound-transmitting material such as an open cell reticulated foam having first and second opposite surfaces 156 and 157, respectively, a generally cylindrical periphery 158 which could alternatively be generally oval, and an axial hole 152 extending between those surfaces 156 and 157. On the second surface 157 of the first layer 151 is centrally affixed (e.g., by thermal bonding, adhesive or mechanical fastening means) a stiff, resiliently deformable attachment member or disc 153 having a through hole or opening 154 which could be similar to or the same as the disc 13 described above. The sleeve assembly 150 is adapted to be mounted on the end portion of a sound control device such as the end portion 110 by inserting its knob-like end part 113 through the opening 154 in the disc 153, either from its side opposite the first layer 151, or, if the material in the first layer 151 will stretch around the knob-like part 113, from its side adjacent the first layer 151. The sound transmitting material forming the first layer 151 can help prevent detritus or cerumen from the ear canal from entering the sound delivery tube of a hearing aid or other sound control device on which sleeve assembly 150 may be mounted. The first layer 151 can, as illustrated, have a portion that extends beyond the disc 103 of sufficient outer diameter and flexibility to bend and assume a generally umbrella-like shape conforming to the generally oval inner surface of an ear canal when the sleeve assembly 150 is inserted into the ear canal on an end portion of a sound control device such as the end portion 110 of FIG. 16. Alternatively, the sleeve assembly 150 could be adapted to be cerumen guard that primarily only prevent detritus or cerumen from the ear canal from entering the sound delivery tube of a hearing aid or other sound control device on which sleeve assembly 150 may be mounted. This could be done by reducing the diameter of the first layer 151 so that it is about the same as, or only slightly larger than, the outer diameter of the disc 153 (e.g., in the size range set out above for the sleeve assembly 100 modified to provide a cerumen guard) in which event its periphery will not make extensive contact with the inner surface of the normal adult ear canal.

Figure 25:
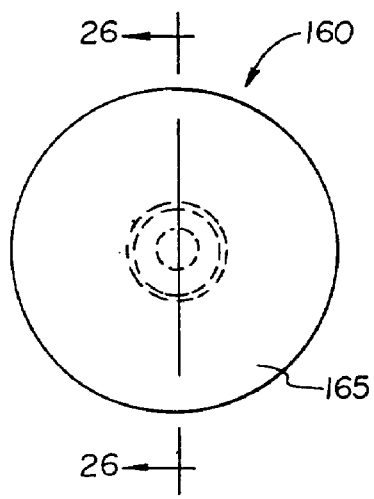
FIG. 25 is an enlarged end view of a ninth embodiment of a sleeve assembly according to the present invention.
Figure 26:
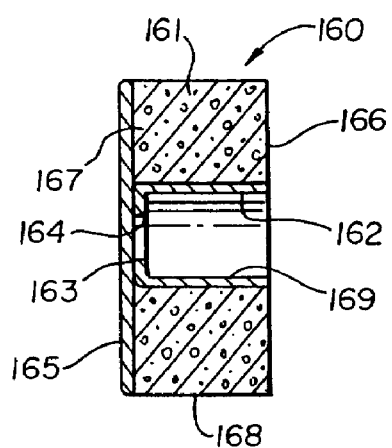
FIG. 26 is a sectional view of the sleeve assembly of FIG. 25, taken approximately along section line 26—26 of FIG. 25 and looking in the direction of the arrows.
Figure 29:
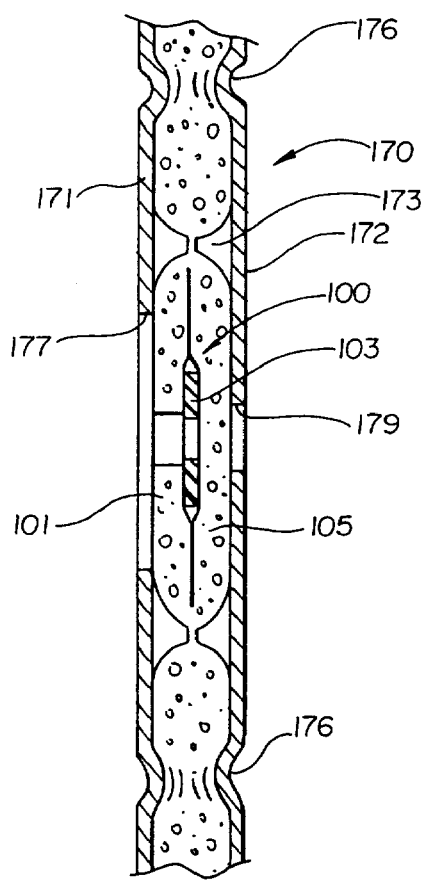
FIG. 29 is an enlarged fragmentary sectional view taken approximately along line 29—29 of FIG. 27 and looking in the direction of the arrows.
Figure 30:
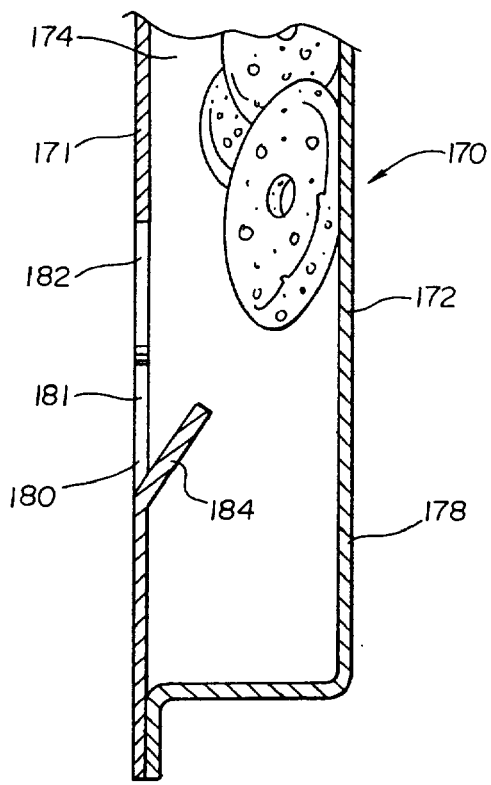
FIG. 30 is an enlarged fragmentary sectional view taken approximately along line 30—30 of FIG. 27 and looking in the direction of the arrows.

FIGS. 25 and 26 of the drawings illustrate a ninth embodiment of a sleeve assembly 160 according to the present invention for removable mounting on an end portion of a sound control device terminating in a knob-like part. The sleeve assembly 160 includes a first layer 161 of resilient polymeric or other suitable material having first and second opposite surfaces 166 and 167, respectively, a cylindrical periphery 168 between those surfaces, and having an axial hole 162 extending between those surfaces 166 and 167. The sleeve assembly 160 further includes an attachment means or member fixed to the first layer 161 for releasably attaching the first layer 161 of foam on the end portion of the sound control device, which attachment member comprises a resilient stiff flexible disc-like part 163 having a through opening 164 aligned with the hole 162 to affording movement of the knob-like part through the hole 162 and the opening 164 in the disc-like part 163 so that the area circumjacent to the opening 164 in the disc-like part 163 can releasably engage the portion of the sound control device to hold the sleeve assembly 160 on the portion of the sound control device. That attachment member further comprises a hollow cylindrical part 169 having opposite axially spaced ends. The disc-like part 163 extends across one of those ends and is integral with the hollow cylindrical part 167, the integral disc-like and hollow cylindrical parts 163 and 167 preferably being integrally made as one piece by vacuum forming a thin uniformly thick sheet of resiliently flexible thermoplastic material. The outer surface of the hollow cylindrical part 169 of the attachment member is attached (e.g., by thermal bonding, by an adhesive such as a heat activateable adhesive coating on the sheet of thermoplastic from which it is formed, or mechanical fastening means) to an inner surface of the first layer 161 that defines the hole 162 between the first and second surfaces 166 and 167 and positions the disc-like part 163 adjacent the second surface of the first layer 161. Overlaying the side of the disc-like part 163 opposite the first layer 161 and having its periphery attached to the second surface 167 of the first layer 161 is a thin layer 165 of a sound-transmitting material or scrim (e.g., reticulated open cell foam) that helps prevent detritus or cerumen from the ear canal from entering the sound delivery tube of a hearing aid or other sound control device on which sleeve assembly 160 may be mounted.

FIGS. 27–30 illustrate a container 170 in which a plurality of the sleeve assemblies 80, 90, 100, 120, 130, 140 or 150 can be similarly contained and which will be described containing a plurality of sleeve assemblies 100. The container 170 is formed from top and bottom sheets of material 171 and 172, respectively (e.g., of 0.024 SBB plastic coated bristle board) having major surfaces attached together, and defining between those major surfaces a first compartment 173 (see, FIG. 29) adapted to receive unused sleeve assemblies 100, and a second compartment 174 (see, FIG. 30) adapted to receive used sleeve assemblies 100. The top sheet 171 has a plurality of holes 177 which are larger than the major diameter of the sleeve assembly 100, but smaller then the diameter of the peripherally joined first layer 101 and layer 105 that envelope the disc 103. The bottom sheet 172 has a plurality of through holes or passageways 179 that are opposed to and centered on the holes 177 in the top sheet 171. The diameters of the passageways 179 are somewhat less than the outer diameter of the discs 103, but somewhat greater than the diameter of the knob-like part 113 of the end portion 110. A plurality of sleeve assemblies 100 are formed by positioning discs 103 between and heat sealing together two sheets of foam to delineate individual sleeve assemblies 100 without physically removing them from the surrounding portions 175 thereof or "weed". The heat sealed sheets are positioned and fastened in the compartment 173 to hold and position the sleeve assemblies 100 they delineate in the proper positions between the holes 177 and 179. The heat sealed sheets are fastened in the compartment 173 by fastening the portions 175 thereof surrounding the sleeve assemblies 100 they delineate to the top and bottom sheets 171 and 172, which can be done with a suitable adhesive or, as illustrated, by heat sealing plastic coating on the sheets 171 and 172 to those portions 177 of the sheets of foam at spaced indented locations 176. To withdraw a sleeve assembly 100 from the compartment 173, the user inserts the knob-like part 113 of the end portion 110 (or a similarly shaped distal end portion of another sound control device) through one of the holes 177 in the top sheet 171 and then through the axial hole 102 in the sleeve assembly 100 below the hole 177. The knob-like part 113 is then pressed through the opening 102 in the disc 103 which is supported by part of the bottom sheet 172 circumjacent the hole 179 below that sleeve assembly 100, and moves into that hole 179. The portion of the disc 103 circumjacent the hole 102 resiliently deforms as the knob-like part 113 passes through it, and then contracts and becomes seated in the groove 114 of the end portion 110. Removal of the end portion 110 through the hole 177 in the top sheet 171 also removes the sleeve assembly 100, which is now mounted on the end portion 110. Effective mounting occurs when the restraining force caused by the positioning of the disc 103 in the groove 114 is greater than the restraining force needed to tear the periphery of the sleeve assembly 100 from the portions 177 of the heat sealed sheets delineating the adjacent sleeve assemblies 100 that are fastened between the sheets 171 and 172 and to pull the sleeve assembly 100 from between the sheets 171 and 172 while deflecting it so that it can pass through the hole 177. If for some reason, sufficient engagement has not been achieved between the disc 103 and the end portion 110, that restraining force will pull the sleeve assembly 100 off of the end portion 110 and cause it to remain in the container 170 as the end portion 110 is pulled from the container 170.

The second compartment 174 adapted to receive used sleeve assemblies 100 is best seen in FIGS. 24 and 26. The bottom sheet 172 has portions folded to form a rectangular projection 178 projecting away from the top sheet 171 to form the compartment 174 for used sleeve assembles therebetween. The top sheet 171 has a through generally keyhole shaped slot 180 to provide means for removing used sleeve assemblies 100 from sound control devices such as the end portion 110 and automatically storing them in the compartment 174. The generally keyhole shaped slot 178 includes a major generally rectangular portion 181, and a smaller rectangular portion 182. The width of the major portion 181 is approximately the same as, or slightly greater than, the major diameter of the sleeve assembly 100, and the width of the rectangular portion 182 is less than the diameter of the disc 103, but greater than the diameter of the first elongate part 11 of the end portion 110 on the side of the groove 114 opposite the knob-like part 113. To remove a sleeve assembly 100 from a sound control device such as the end portion 110 on which it is mounted, the sleeve assembly 100 on the end portion 110 is inserted through the major portion 181 of the slot 180 whereupon the end portion 110 is slid transversely into the rectangular portion 182 of the slot 180. The end portion 110 is then pulled away from the top sheet 171, the resultant force causing the portion of the disc 103 circumjacent the hole 102 to spring away and allow the sleeve assembly 100 to be pulled off of the end portion 110 and deposited in the compartment 174. The top sheet 171 includes a rectangular portion 184 projecting into the rectangular portion 181 of the slot 180 to restrict movement of used sleeve assemblies 100 in the compartment 174 out through that rectangular portion 181.

If desired, the container 170 may be provided with a lid, shrink wrapped, or packaged in a cardboard sleeve.

Figure 31:
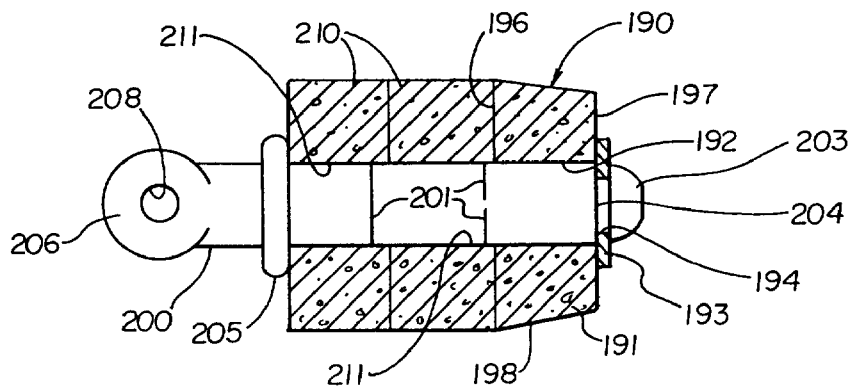
FIG. 31 is a longitudinal-sectional view of a tenth embodiment of a sleeve assembly according to the present invention mounted on a sound control device.

Referring now to FIG. 31 of the drawings, there is illustrated a tenth embodiment of a disposable sleeve assembly 190 according to the present invention releasably engaged with an end portion of a reusable solid sound control device or ear plug 200. The ear plug 200 is elongate, smaller in diameter than the ear canal, preferably of a stiff resilient flexible polymeric material (e.g., polypropylene) and has two axially spaced sets 201 of two opposed transverse cuts in each set 201, with the opposed transverse cuts in each set 201 extending not quite half way through the plug 200 to form between them a flexible portion of the plug 200 of the type called a "living hinge". The "living hinges" formed by the two sets 201 of opposed transverse cuts are disposed at right angles to each other with respect to a cross-section of the plug, and thus, allow the plug 200 to bend in different directions at those "living hinges" into a shape generally corresponding to the tortuosity of the ear canal into which it is inserted. The sleeve assembly 190 includes a first layer 191 of sound attenuating resilient slow recovery closed cell foam having first and second opposite surfaces 196 and 197, respectively, a frusta-conical periphery 198 between those surfaces 196 and 197, and an axial hole 192 extending between those surfaces 196 and 197. On the second surface 197 of the first layer 191 is affixed (e.g., by thermal bonding, adhesive, or mechanical fastening means) a stiff, resiliently deformable attachment member or disc 193 having a through opening 194 which could be similar to or the same as the disc 13 described above. The opening 194 is axially aligned with the hole 192 and is about the same size or slightly smaller than the hole 192. The end portion of the plug 200 has a knob-like part 203 at its distal end partially defined by an annular circumferential groove 204 at the proximal end of the knob-like part 203. In use, the knob-like part 203 is inserted through the axial hole 192 in the first layer 191 from its first surface 196 and moved into contact with the portion of the disc 193 surrounding its opening 194. Axial force is then applied so that the portion of the disc 193 circumjacent its opening 194 yields slightly, allowing the knob-like part 193 to pass through the opening 194. The circumjacent portion of the disc 193 then springs back, seating itself in or engaging the groove 204 to provide a snap fit that securely engages the sleeve assembly 190 on the plug 200. Alternately, as illustrated, two cylindrical layers 210 of sound attenuating resilient slow recovery closed cell foam having axially extending through openings 211 are mounted on the plug 200 on the side of the sleeve assembly 190 opposite the disc 193 to extend the length of foam that can contact the inner surface of an ear canal and to facilitate bending of the plug 200 at the "living hinges" to correspond to the tortuosity of an ear canal into which it is inserted. Although, the plug 200 has an annular radially outwardly projecting shoulder 205 to insure that the sleeve assembly 190 and the cylindrical layers 210 will be maintained in a fixed location on the plug 200. The plug 200 also includes a manually engageable tab 206 at its end opposite the knob-like part 203 by which it may be manually manipulated to insert it in or remove it from an ear canal. The tab 206 has a through opening 208 that can receive a cord (not shown) by which two of the ear plugs 200 can be tied together.

In view of all such and other obvious variations of the invention, the following claims should be construed with full appreciation for and recognition of the doctrine of equivalents.

What is claimed:

1. A sleeve assembly for removable mounting on a portion of a sound control device including a knob-shaped part, said sleeve assembly comprising a first layer of resilient flexible material having opposite first and second surfaces, and a stiff flexible attachment member fixed to said first layer along said second surface, said attachment member having a through opening affording movement of the knob-shaped part through said attachment member so that the area adjacent to the opening in the attachment member can releasably engage the portion of the sound control device to hold the sleeve on the sound control device.

2. A sleeve assembly according to claim 1 wherein said first layer is of polymeric material and has a periphery between said first and second surfaces adapted to conform to the ear canal of a user into which the sleeve assembly is inserted, and said first layer has a hole between said first and second surfaces aligned with the opening in said attachment member or is readily penetrable adjacent the opening in said attachment member to afford movement of the knob-shaped part of the sound control device through said first layer and said attachment member.

3. A sleeve assembly according to claim 2 wherein the periphery of said first layer has a shape selected from the group consisting of cylindrical, oval, truncated conical, contoured, lobed, and fluted.

4. A sleeve assembly according to claim 2 wherein said first layer is of sound attenuating slow recovery foam.

5. A sleeve assembly according to claim 2 further including a layer of sound transmitting cerumen restricting material over the side of the attachment member opposite said first layer, said layer of sound transmitting cerumen restricting material having a peripheral portion attached to said first layer.

6. A sleeve assembly according to claim 2 wherein said first layer of material is thin and flexible, and said sleeve assembly further includes a thin flexible layer of sound transmitting cerumen restricting material extending over the side of the attachment member opposite said first layer and having a periphery attached to the periphery of said first layer, said first layer and said layer of sound transmitting cerumen restricting material having sufficient outer diameters and being sufficiently flexible to bend and assume a generally umbrella-shaped shape having a peripheral portion conforming to a generally oval inner surface of an ear canal when the sleeve assembly is inserted into that ear canal on the end portion of the sound control device.

7. A sleeve assembly according to claim 6 wherein said attachment member includes resiliently flexible spaced radially projecting lobe-shaped portions between said first layer and said layer of sound transmitting cerumen restricting material.

8. A sleeve assembly according to claim 6 wherein said first layer and said flexible layer of sound transmitting material are attached together along radially extending lines between said attachment member and said peripheries.

9. A sleeve assembly according to claim 6 further including a layer of water absorbent or adsorbent material between said first layer and said layer of sound transmitting cerumen restricting material.

10. A sleeve assembly according to claim 1 wherein said first layer is of sound transmitting cerumen restricting material and has a sufficiently large outer diameter to contact and conform to the car canal of a user into which the sleeve assembly is inserted.

11. A sleeve assembly according to claim 1 wherein said first layer is of sound transmitting cerumen restricting material and has a sufficiently small outer diameter to restrict contact with the ear canal of a user into which the sleeve assembly is inserted.

12. A sleeve assembly according to claim 1 wherein said first layer has a hole between said first and second surfaces aligned with the opening in said attachment member or is readily penetrable adjacent the opening in said attachment member to afford movement of the knob-shaped part of the sound control device through said first layer and said attachment member, and said sleeve assembly further includes a thin flexible layer of sound transmitting cerumen restricting material extending over the side of the attachment member opposite said first layer and attached to said first layer, said layers having a sufficiently small outer diameter to restrict contact with the ear canal of a user into which the sleeve assembly is inserted.

13. A container containing a plurality of the sleeve assemblies of claim 1, said container comprising a first compartment for containing the sleeve assemblies including an upper sheet having a plurality of through holes, a bottom sheet having passageways that are directly below the holes, the diameters of the passageways being somewhat less than the outer diameter of the attachment members of the sleeve assemblies and the attachment members of the sleeve assemblies being supported by the parts of the bottom sheet circumjacent the passageways below the sleeve assemblies, said container including means for restricting removal of the sleeve assemblies by inserting a portion of a sound control device including a knob-shaped part through a attachment member of one of the sleeve assemblies and withdrawing the sound control device from the container if a desired degree of engagement has not been achieved between the knob shaped part of the sound control device and the sleeve assembly, whereupon the sleeve assembly will slip off the sound control device and remain in the container.

14. A container according to claim 13 wherein said holes are in part defined by radially inward extending finger like portions of said to sheet, the distal ends of said finger like portions defining central portions of said holes having diameters slightly less than the diameters of the first layers of the sleeve assemblies so that the finger like portions must be flexed to allow the first layers of the sleeve assemblies to pass through the holes to provide said means for restricting removal of one of the sleeve assemblies with the knob shaped part of the sound control device if a desired degree of engagement has not been achieved between the sleeve assembly and the sound control device.

15. A container according to claim 13 wherein said sleeve assemblies are frailly attached to a portion of said container, said friable attachment being breakable only after application of a predetermined force to allow the sleeve assemblies to pass through the holes to provide said means for restricting removal of one of the sleeve assemblies with the knob shaped part of the sound control device if a desired degree of engagement has not been achieved between the sleeve assembly and the sound control device.

16. A container according to claim 13 further comprising a second compartment for containing used sleeve assemblies including a sheet having a through generally key-hole shaped hole, said key-hole shaped hole including a major portion and a smaller portion, the size of the major portion being at least the size of the first layer of the sleeve assembly, and the smaller portion having a width dimension less than the diametrical dimension of the attachment member, a sleeve assembly being removable from a sound control device on which it is mounted by inserting the sleeve assembly on the sound control device through the major portion of the hole, sliding the sound control device into the smaller portion of the hole, and pulling the sound control device away from the sheet to cause the sleeve assembly to be pulled off of the sound control device and left in the second compartment.

17. A sleeve assembly for removable mounting on an end portion of a sound control device including a knob-shaped part, said sleeve assembly comprising a first layer of resilient flexible polymeric foam having opposite first and second surfaces, a periphery between said first and second surfaces adapted to conform to the ear canal of a user into which the sleeve assembly is inserted, and a hole between said first and second surfaces, and said sleeve assembly further comprising attachment structure for releasably attaching the first layer of foam on the end portion of the sound control device comprising a resilient stiff flexible disc-shaped part fixed to said first layer and having a through opening aligned with said hole to affording movement of the knob-shaped part through said hole and said opening in said attachment member so that the area circumjacent to the opening in the attachment member can releasably engage the portion of the sound control device to hold the sleeve assembly on the portion of the sound control device.

18. A sleeve assembly according to claim 17 wherein said first layer comprises sound attenuating slow recovery foam.

19. A sleeve assembly according to claim 17 wherein said attachment structure further comprises a hollow cylindrical part having opposite axially spaced ends, said disc-shaped part extending across one of said ends and being integral with said hollow cylindrical part, said hollow cylindrical part being attached to a surface of said first layer defining said hole between said first and second surfaces and positioning said disc-shaped part adjacent said second surface of said first layer.

20. A sleeve assembly according to claim 17 further including a layer of sound transmitting cerumen restricting material extending over the disc-shaped part and having a peripheral portion attached to the second surface of said first layer.

21. A sleeve assembly according to claim 17 wherein said disc-shaped part extends along and is attached to said second surface of said first layer and said sleeve assembly further includes a layer of sound transmitting cerumen restricting material extending over said disc-shaped part and having a peripheral portion attached to the second surface of said first layer.

22. In combination, a portion of a sound control device including a knob-shaped part, and a sleeve assembly comprising a first layer of resilient foam having opposite first and second surfaces, and a stiff flexible attachment member having a through opening fixed to said first layer along said second surface, said portion of the sound control device extending through said attachment member with the area adjacent to the opening in the attachment member releasably engaging the sound control device to hold the sleeve on the sound control device.

23. A combination according to claim 22 wherein said portion of the sound control device is a sound delivery tube having a through sound passageway opening through said knob-shaped part, said first layer is of polymeric foam and has a periphery between said first and second surfaces adapted to conform to the ear canal of a user into which the sleeve assembly is inserted, said first layer has a hole between said first and second surfaces aligned with the opening in said attachment member through which the sound delivery tube extends with said knob-shaped part on the side of the attachment member opposite the first layer, and the sleeve assembly further includes a layer of sound transmitting cerumen restricting material over the side of the attachment member opposite said first layer and overlaying said knob-shaped part, said layer of sound transmitting cerumen restricting material having a peripheral portion attached to said first layer.

24. A combination according to claim 23 wherein said first layer is of sound attenuating slow recovery film.

25. A combination according to claim 22 wherein said portion of the sound control device is a sound delivery tube having a through sound passageway opening through said knob-shaped part, said first layer is of thin flexible polymeric material, said first layer has a hole between said first and second surfaces aligned with the opening in said attachment member through which the sound delivery tube extends with said knob-shaped part on the side of the attachment member opposite the first layer, and the sleeve assembly further includes a layer of sound transmitting cerumen restricting material having a peripheral portion attached to said first layer, said first layer and said layer of sound transmitting cerumen restricting material having sufficient outer diameters and being sufficiently flexible to bend and assume a generally umbrella shape having a peripheral portion conforming to the generally oval inner surface of an ear canal when the sleeve assembly is inserted into that ear canal on the end portion of the sound deliver tube.

26. A combination according to claim 25 wherein said attachment member includes resiliently flexible spaced radially projecting lobe-shaped portions between said first layer and said layer of sound transmitting cerumen restricting material.

27. A combination according to claim 25 wherein said first layer and said flexible layer of sound transmitting material are attached together along radially extending lines between said attachment member and said peripheries.

28. A combination according to claim 25 wherein said sleeve assembly further including a layer of water absorbent or adsorbent material between said first layer and said layer of sound transmitting cerumen restricting material.

29. A combination according to claim 22 wherein said portion of the sound control device is a sound delivery tube having a through sound passageway opening through said knob-shaped part, said first layer is of sound transmitting cerumen restricting material and has a sufficiently small outer diameter to restrict contact with the ear canal of a user into which the sleeve assembly is inserted, and said knob-shaped part is positioned on the side of the attachment member adjacent the first layer.

30. A combination according to claim 22 wherein said portion of the sound control device is a sound delivery tube having a through sound passageway opening through said knob-shaped part, said first layer has a hole between said first and second surfaces aligned with the opening in said attachment member through which the sound delivery tube extends with said knob-shaped part on the side of the attachment member opposite the first layer, and the sleeve assembly further includes a layer of sound transmitting cerumen restricting material over the side of the attachment member opposite said first layer and overlaying said knob-shaped part, said layer of sound transmitting cerumen restricting material having a peripheral portion attached to said layers having sufficiently small outer diameter to restrict contact with the ear canal of a user into which the sleeve assembly is inserted.

31. A combination according to claim 22 wherein said portion of the sound control device is a solid plug, said first layer is of sound attenuating slow recovery polymeris foam and has a periphery between said first and second surfaces adapted to conform to the ear canal of a user into which the sleeve assembly is inserted, and said first layer has a hole between said first and second surfaces aligned with the opening in said attachment member through which the portion of the sound device extends with said knob-shaped part on the side of the attachment member opposite the first layer.

* * * * *

UNITED STATES PATENT AND TRADEMARK OFFICE
CERTIFICATE OF CORRECTION

PATENT NO.   : 6,310,961 B1
DATED        : October 30, 2001
INVENTOR(S)  : Robert J. Oliveira et al.

It is certified that error appears in the above-identified patent and that said Letters Patent is hereby corrected as shown below:

<u>Column 18, claim 10,</u>
Line 59, delete "car" and insert therefore -- ear --.

<u>Column 22, claim 30,</u>
Line 20, after "said" and before "layers" insert -- first layer, and said --.

Signed and Sealed this

Twenty-sixth Day of March, 2002

Attest:

JAMES E. ROGAN
Attesting Officer    Director of the United States Patent and Trademark Office